United States Patent [19]

Nuwayser et al.

[11] Patent Number: 4,623,588
[45] Date of Patent: Nov. 18, 1986

[54] CONTROLLED RELEASE COMPOSITE CORE COATED MICROPARTICLES

[75] Inventors: Elie S. Nuwayser, Wellesley; William A. Nucefora, Bedford, both of Mass.

[73] Assignee: Biotek, Inc., Woburn, Mass.

[21] Appl. No.: 803,733

[22] Filed: Dec. 2, 1985

Related U.S. Application Data

[62] Division of Ser. No. 577,079, Feb. 6, 1984, Pat. No. 4,568,559.

[51] Int. Cl.[4] .......................... A61K 9/30; A61K 9/50; A61K 9/58; B05D 7/02
[52] U.S. Cl. .................................. 428/402.24; 424/31; 424/35; 427/3; 427/213
[58] Field of Search ............... 424/31, 35; 427/3, 213; 428/402.24

[56] References Cited

U.S. PATENT DOCUMENTS 3,089,824 5/1963 Wurster .................................. 424/35
4,568,559 2/1986 Nuwayser et al. ..................... 427/3

Primary Examiner—John E. Kittle
Assistant Examiner—Mukund J. Shah
Attorney, Agent, or Firm—Richard P. Crowley

[57] ABSTRACT

A process for preparing coated microparticles, which process comprises preparing a solvent solution of an active ingredient to be encapsulated and a film-forming polymer, removing the solvent to provide a dry, composite, uniform admixture of the active ingredient and the polymer material, reducing the composite admixture to a defined smaller particle size distribution, coating the reduced composite core particles in a fluidized bed, with a uniform defined wall thickness of the same or substantially the same film-forming polymer material to provide composite core coated microparticles.

9 Claims, 2 Drawing Figures she
CONTROLLED RELEASE COMPOSITE CORE COATED MICROPARTICLES The invention described and claimed hereunder was reduced to practice with the support of the U.S. Government under NIH Contract No. NO1-HD-0-2847 and the U.S. Government has a nonexclusive license to practice the invention on behalf of the United States.

This is a continuation of co-pending application Ser. No. 577,079 filed on Feb. 6, 1984, now U.S. Pat. No. 4,568,559.

BACKGROUND OF THE INVENTION

Fluidized bed coating processes are well known and typically employ a fluidized bed dryer to coat discrete, finely-divided particles while the particles are suspended in an upwardly-moving gas stream in a coating chamber. While so suspended, a solution of the coating material is sprayed into the moving fluid bed of particles and the particles subsequently dryed and recovered, the recovered particles contain generally a thin coating of the coating material thereon. Fluidized bed dryers are commercially sold as standard pieces of engineering equipment and typical Wurster-type dryers and processes are described; for example, in U.S. Pat. Nos. 3,117,027, 3,196,827, 3,253,944, 2,648,609, 2,799,241, and 3,241,520. These patents disclose various fluidized bed dryers for the encapsulation of discrete particles with various coatings and various processes for coating such discrete particles in a fluidized bed technique.

One technique for the fluidized bed coating of discrete particles comprises suspending seed particles or crystals of about 20–200 mesh particle size or smaller of the particular material to be coated, such as a drug, in a fluidized bed chamber and, thereafter, contacting the suspended particles in the bed with an atomized mixture of a granulating material, so as to build up the seed particles to the desired size granules. The granulating materials are typically dispersed, dissolved or suspended in a volatile liquid such as water or an organic solvent and sprayed into the fluidized bed in a technique such as set forth in U.S. Pat. No. 3,089,824, issued May 14, 1963. Another technique of preparing agglomerate-type particles typically for subsequent use with tablets comprises employing a mixture of finely-divided powders in a fluidized bed and a solution of binder material is used to adhere the fine particles in the bed into larger particles, such as, for example, as described in U.S. Pat. No. 3,207,824, issued Sept. 21, 1965.

The coating of finely-divided particles in a fluidized bed provides for microencapsulation and may use a wide variety of discrete particles to be coated with a wide variety of materials to be deposited as a uniform coating layer on the particles. Encapsulating ingredients useful in fluidized bed coatings include but are not limited to waxes; cellulose such as ethyl cellulose, hydroxy ethyl and propyl cellulose and methyl cellulose, and carboxymethyl cellulose; gelatins; gums; fatty acids like stearates; and natural and synthetic film-forming polymrs such as shellac, starches, fluorocarbons, polyvinyl alcohol, polyvinyl acetate, vinyl chloride resins, acrylic resins, etc. The coating ingredients may be used as solvent or aqueous solutions, emulsions, dispersions, and melts. Materials capable of being employed in a fludized bed include finely-divided solid material to be microencapsulated. Microencapsulation has been used for the encapsulation of pigments, in paint making, in paper making, in food products, pharmaceuticals, for beauty aids, laundry products, pressure-sensitive copying systems, paper coatings and a wide variety of other uses. In particular, it has been found that the microencapsulation technique is particularly useful for the encapsulation coating of materials, such as drugs, in order to provide a uniform coating and therefore provide for a delayed or controlled release of the active ingredient from the coated microcapsule. Microencapsulation techniques are set forth, for example, generally in *Chemical Technology Review*, No. 73, entitled "Microcapsulations and Microcapsulation Techniques" (1975), and *Chemical Technology Review*, No. 135, entitled "Microcapsules and other Capsules Advances Since 1975," both published by the Noyes Data Corporation.

SUMMARY OF THE INVENTION

This invention relates to coated microparticles and a method of preparing such coated microparticles. In particular, the invention concerns a process of preparing coated microparticles in a fluidized bed, the microparticles comprising a core material composed of a coated ingredient and a coating material, and coated with a film-forming polymer and to a composite core microparticles so prepared.

The invention comprises a process for preparing coated microparticles by a fluidized air bed technique, which microparticles are composed of a composite core material and a film-forming material uniformly coated on the core material. The composite core material employed comprises one or more active ingredients which are designed to be placed in microparticle form and typically comprises an active drug or other material which is to be delivered in a delayed or controlled release manner and a film-forming polymer.

The microparticles of the invention comprise composite core material having a uniform coating of defined thickness, with the very-finely-divided composite core material having a film-forming polyer material as the coating, which film-forming polymer material is the same or of substantially the same as the film-forming material employed in preparing the composite core material. The coated microparticles of the invention may be of any desired particle size; however, typically the control microparticles comprises particles of generally less then 1000 microns and typically less than about 200 microns, for example, 5–100 microns, particularly where the coated microparticles of the invention are to be employed for the uniform or controlled delivery of an active ingredient, such as a drug, into the tissues of a patient either in capsule, tablet, or injectable liquid form.

In general, the process of the invention for preparing the microparticles comprises preparing a solvent solution of the active ingredient of the microparticles and a film-forming polymer material and removing the solvent to provide a dry, composite, generally-uniform admixture of the active ingredient and the polymer material. The active ingredient in the core material may comprise one or more ingredients and may vary in amount and range for example from 5% to 95% by weight, such as 20% to 80% by weight. The process permits major amounts of the active ingredient to be used in the core, for example, 60% to 90%. The core material may include, besides the coating polymer or material, other materials as additives, such as binders, adhesives, fillers, etc.

The dry, composite core material is reduced in size to provide composite core particles of a fine, low particle size distribution, which size distribution is the same or generally slightly less than the particle size distribution of the desired coated microparticles to be prepared by the process. The reduced composite core particles are then coated in a fluidized bed with a generally-uniform defined wall thickness of the same or substantially the same film-forming polymer as used to prepare the composite core material. The coated core particles are prepared by suspending the composite core particles in an air stream in a fluidized bed and atomizing or spraying a film-forming polymer or coating solution over the suspended composite core particle in the fluidized bed to provide a dry, uniform coating thereon. The recovered coated microparticles of the process are of carefully defined particle size range and are uniformly coated with the film-forming coating polymer. The process provides for a significant improvement in both the yield of the microparticles and in the uniformity of the coating providing for significant advantages in the quality and quantity of the coated microparticles and in the cost of operating the process and in preparing such coated microparticles.

In one embodiment the invention comprises a process for preparing coated microparticles containing a drug as an active indgredient, the coated microparticles less than about 200 microns, and suitable for use for injecting into living tissue to provide for the control or delayed release of the drug-active ingredient. The process than comprises preparing a volatile organic solution or water solution or emulsion of the active drug ingredient and a synthetic film-forming polymer material. The synthetic film-forming polymer material comprises a pharmaceutically or inert material and more preferably, a biodegradable natural or synthetic polymer material, such as a polylactide, a glycolide copolymer thereof.

The drug-active ingredient may comprise a wide variety of materials or combinations and be selected for the particular therapeutic function desired. Preferably, the active-drug ingredient does not react with and is chemically inert with the synthetic film-forming polymer material. The solution solvent is then removed to provide a generally dry composite uniform admixture of the active ingredient and the polymer material. The dry, composite admixture is then sieved to particles of a defined particle size distribution and typically lastly the particles should be ground and then sieved to the same or generally slightly less than the particle size distribution of the desired coated microparticles, generally less than 1000 microns and typically where the coated microparticles are to be employed for pharmaceutical injection purposes, less than 200 microns. Thereafter, the reduced composite core microparticles are placed in a fluidized bed dryer, such as a commercial Wurster dryer, suspended in an air stream and then sprayed in fluidized bed form with a liquid, generally a solution of the same film-forming polymer material, usually in a volatile organic or water solution to provide a substantially uniform coating on the microparticles. Thereafter the coated microparticles containing the core coated materials are removed from the fluidized bed dryer and employed as desired.

The process of the invention produces large quantities of very small, coated particles (generally less than 200 micrometers in diameter) from any type of particle having any geometric shape. Unlike microcapsules, the coated microparticles can be compressed into tablets, pellets, or other shapes without breakage or significant loss in their integrity and the fine coated microparticles can be placed in a liquid carrier and injected into tissue. The particles can be used for oral administration for the controlled release of drugs and, for example, can be injected into the body of a patient by means of a small hypodermic needle. Because of the precision and uniformity of the wall coating, the microparticles deliver a constant and sustained dose of their content to the tissue for periods ranging from several hours to several years.

The process provides for the preparation of microparticles with a wall coating which is uniformly applied to all surfaces of the material thus producing a delivery rate of the active ingredient which is constant and sustained for long and defined time periods. The process provides microparticles with a wall coating whose thickness can be precisely adjusted and tailored to deliver the active ingredient, for example, a drug, over a wide range of delivery periods. It is well established that wall uniformity controls the constancy and decay of the rate of drug release, whereas wall thickness controls the relative amount or dose delivered and the duration of constant delivery. The wall coating thickness may be varied as desired, but typically would range from about 0.1 to 20 microns; for example, 1 to 5 microns.

Coated microparticles for controlled drug release, particularly injectable microparticles, must meet certain important criteria as to acceptable size, biodegradability, and rate of drug release. The process is uniquely successful in preparing microparticles from any drugs coated with many types of materials and polymers, especially with a class of biodegradable polymers of the type known as polylactide, polyglycolide, and various copolymers of lactide and glycolide. For example, coated microparticles prepared from the steroid known as levonorgestrel and coated with poly-L(−)lactide polymer and then injected intramuscularly in rabbits, were able to maintain a constant level of the drug in the blood of the rabbit for periods exceeding 250 days. After the drug is completely released, the biodegradable polymer is slowly metabolized by the tissue.

Importantly, the process produces microparticles which are completely covered by the coating material and with a precise and uniform coating thickness of the coating material on all the surfaces of the composite core material being coated. This is essential if uniform delivery of the drug must be maintained for long time periods. A further advantage of the process is the significant improvement in the yield of coated particles in any desired size range (especially important in the less than 200 micron injectable range). This improvement results from reducing the losses produced by particle agglomeration, by core particle breakage, by fragmentation, and by separation of the film-forming wall coating from the composite core particles because of poor bonding between the two materials.

The process involves the use of fluidized bed processes to prepare the core/wall coated microparticles ranging in size from a few microns to more than 1000 microns in diameter. In constrast to other processes which produce micropheres composed of a dispersion of the drug in a polymer, the process produces coated particles composed of a discrete composite core material surrounded by a coating wall which is distinguishable from the core and has a measurable thickness. The coated particles are characterized by their unique and highly desirable ability to deliver the drug at a constant "zero order" rate over long periods; whereas other coated micropheres often deliver the drug at an exponential and decaying "first order" rate which has a limited short duration. The microparticles of the process are also characterized by a uniform wall which is tightly bound to the core by virtue of a chemical bond between it and the same or chemically similar film-forming coating materials premixed with and dispersed in the core material. The core may be composed of pure materials or mixturs of materials including drugs, polymers, biologicals, chemicals, reagents, proteins, nucleic acids, living cells, and other compounds capable of being coated in a fluidized bed process. The outer wall coating or shell may be composed of one or more film-forming polymers or other material useful as a coating material.

In preparing microcapsules from drugs using standard and accepted microencapsulation procedures, it has been found that the yield of microcapsules of a specific size is very poor. These standard microencapsulation procedures depend on either coacervation or coagulation, which as such are unable to control either the thickness or the uniformity of the capsule wall. Although these processes control capsule size, there is no evidence of good bonding between the wall and the encapsulated active ingredient. Furthermore, if the appropriate solvents for the polymer and the drug are not available, the final product is a microphere in which the drug is dispersed in the coating polymer. This results in nonzero order (nonlinear and nonuniform) release of the drug.

Although fluidized bed coating processes are well known, such processes have not been succssfully applied to the preparation of coated microparticles in the injectable size region (1–200 microns) especially using biodegradable polymers such as the polylactides, polyglycolides, and their copolymers or other inert pharmaceutical coating material such as cellulosic materials. Most materials, especially drugs, are usually available only in micronized or crystalline form. In the micronized form each particle is only a few microns in diamter. It has been found that coating micronized materials in a fluidized bed system results in extremely poor yields of coated particles and large quantities of non-uniform agglomerates of partially coated particles. The agglomerates are formed early in the coating process and grow as the coating proceeds. Ultimately the coating process fails because the agglomerates become too large and cannot be adequately fluidized in the bed. The yield of coated particles formed with micronized materials is very poor especially in the below 1000 micron range. If on the other hand larger drug crystals are used for coating instead of micronized material, the crystals fragment and become micronized very early during the coating process, and ultimately form agglomerates similar to those formed with micronized materials.

The process of the invention avoids the difficulties of the prior art and produces significant improvement in both the yield of microcapsules and in coating uniformity. The process involves several important individual steps, each of which improves the quality and quantity of usable microcapsules produced. The process steps, taken in combination, produce a significant improvement in microcapsule yield and coating uniformity and in the economics of the process.

In the process, the active ingredient, for example, the drug, and coating or wall material (that is, the polymer which is used to encapsulate the drug) are mixed together with a solvent. The amounts and ratios used of the two components is dependent on the final drug concentration desired in the microcapsules. The two components and the solvent are thoroughly mixed until a uniform mixture is formed. Next the excess solvent is removed by evaporation either at standard temperature and pressure or under a partial vacuum. After removing the residual solvent, by heat, the dry residue is ground to a size range equivalent to the size range of the coated particle. The fines are removed by sieving and washing.

Some important steps of the process are preparing a mixture of the active ingredient and the caoting polymer; grinding the mixture to form composite core particles; selecting for further coating those composite core particles which are in the same size range as the desired coated microparticles; washing of the core particles to remove completely all fines; coating the washed composite core particles with the coating polymer using appropriate coating conditions; and isolating and washing the particles in the desired size range. It is essential that the composite core material particles be a uniform dispersion of the coating polymer in the drug core; and have a uniform particle size distribution; and starting dimensions prior to fluidized bed coating which are the same or slightly smaller than the desired coated particles.

The dispersion of the wall coating polymer or its equivalent in the core drug particle improves the mechanical properties of the core by significantly minimizing attrition caused by particle breakage during coating; and improves adhesion between the coating polymer and the composite core. The increase in adhesion or bonding is especially important when both drug and coating material are hydrophobic, as is the case with steroid-type drugs and wall coating polymer materials, for example, made from polylactide, polyglycolide and their copolymers. The composite core material provides for quick and uniform spreading of the coating material on the particle surface with immediate formation of a dry, non-tacky film which reduces the formation of agglomerates.

One important advantage of the process is that no addivites other than the drug, coating polymer, and solvent are needed to obtain high yields of uniformly coated particles, although other additives may be employed if desired. This is important since it significantly reduces the need for performing extensive, costly, and extended toxicological studies in both animals and in humans of the coated microparticle if it is intended for human use. This is illustrated in the levonorgestrel/polylactide coated microparticles since both levonorgestrel and polylactide have been approved for human use by the U.S. Food and Drug Administration.

Another advantage of the process is that the wall coatings can be applied to spherical particles and particles with any geometrical shape. Unlike microcapsules, the coated microparticles which have irregular shapes can be compressed into tablets, pellets, or other shapes without breakage or significant los of their drug release characteristics.

The invention will be described for the purposes of illustration only in connection with certain embodiments; however, it is recognized that those persons skilled in the art may make various changes, additions and modificatons to the invention as described and illustrated, all falling within the spirit and scope of the invention.

DESCRIPTION OF THE EMBODIMENTS

Figure 1:
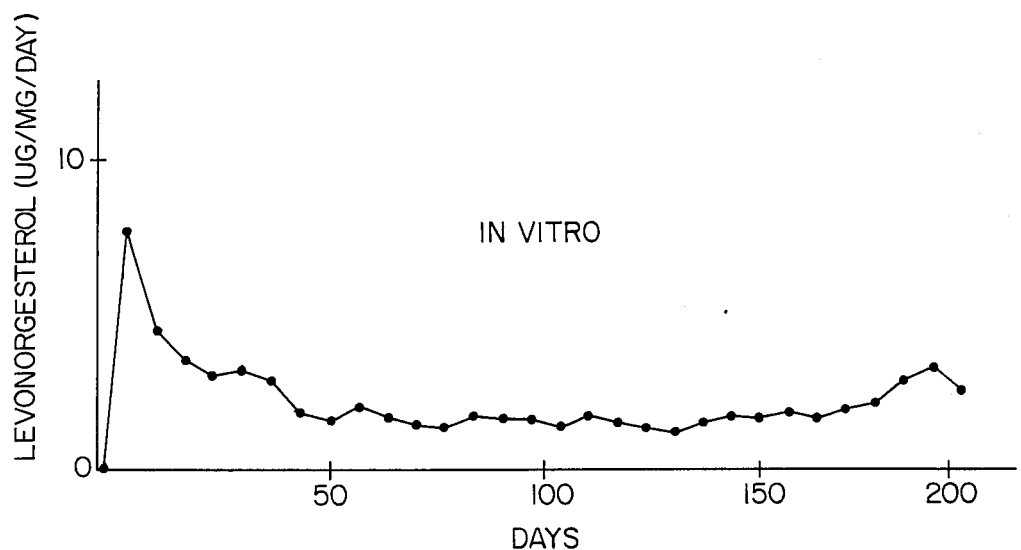
FIG. 1 is a graphical representation of the in vitro release of the steroid drug levonorgestrel from coated microparticles prepared by the process of the invention.

The process of the invention will be illustrated by the use of an active steroid drug levonorgestrel as the active ingredient and a biodegradable polymer poly-L(—)lactide as the synthetic film-forming polymer. The process involves the steps of the preparation of the levonorgestrel core material, the preparation of the polylactide coating solution, the preparation of the levonorgestrel-coated microcapsules in a fluidized bed; and the post treatment of the coated microcapusles and the testing of the coated microcapsules in vivo and in vitro.

The preparation of the composite core material involves preparing a slurry of levonorgestrel and poly-L(—)lactide, and grinding the dried cakes to a specific size fraction for the desired and proper flow properties need to encapsulate the composite core material in the Wurster apparatus for fluid bed coating.

PROCEDURE FOR PREPARATION OF LEVONORGESTREL CORE MATERIAL

1. Weigh out 55 grams of poly-L(—)lactide with a reduced specific viscosity (R.S.V.) of approximately 1 dl/g.
2. Dissolve the poly-L(—)lactide in 560 ml of reagent grade methylene chloride and filter to provide a polymer solution.
3. Weigh out 500 grams of levonorgestrel.
4. Mix the levonorgestrel into the polymer solution in 50 g increments, mixing the powder until a uniform mixture is obtained before adding the next 50 grams.
5. Once all the powder is added, the slurry should be a creamy-type slurry.
6. Pour the slurry into a 9×11 glass casting dish.
7. Allow the slurry to air dry in a hood.
8. Place the casting in the drying oven set at 80° C. for one-half hour to drive out excess methylene chloride.
9. Allow the dry casting to cool.
10. Place all the casting material in a large porcelain mortar and pestle and breakup the casting.
11. Grind the casting in a Bantam Mikro Pulverizer using appropriate hammers and screens until all the material is less than 500 microns.
12. Place the less than 500 micron material in at ATM sonic sifter and remove the 150 micron material.
13. Regrind the material greater than 150 microns.
14. Repeat the last two steps until all the material is lss the 150 microns.
15. Wet sieve the 106–150 micron material over a 106 micron 8-inch sieve as follows: fill a Millipore jet spray apparatus with five gallons of distilled water and pressurize the system to 50 psig; add 200 ml of distilled water to a beaker; add 50 grams of the ground material to the beaker and stir to wet the composite core material; pour the wetted material through the 106 micron sieve and collect the effluent; spray the wetted material with the Millipore apparatus for five minutes; remove the washed material and place it in a glass dish; and repeat until all material is wet sieved.
16. Place the wet material in the drying oven set at 80° C. for 16 hours or until dry.

The preparation of the polymer solution involves dissolving a known amount of the coating polymer, for example, polylactide, into a solvent or solvent-diluent solution, for example, reagent grade methylene chloride, filtering the solution to remove particulates, assaying the concentration of the final polymer solution and adjusting the concentration to 2.5 w/v%.

PROCEDURE FOR PREPARATION OF POLYLACTIDE COATING SOLUTION

1. Weigh out 25 grqms of poly-L(—)lactide.
2. Dissolve it in 1000 ml of methylene chloride.
3. Set up the Millipore filter apparatus and set the regulator pressure to 20 psig.
4. Add 300 ml of polymer solution to the Millipore filter apparatus and filter the polymer solution at 20 psig.
5. Repeat the previous two steps until polymer solution is filtered.
6. Repeat steps 1 through 5 if more than 1000 ml of solution is required, that is, for 500 grams core material about 2000 ml of polymer solution is needed

PROCEDURE FOR PREPARATION OF LEVONORGESTREL MICROPARTICLES

General procedures related to the preoperation and operation of a 6" Wurster air-suspension coater manufactured by Wisconsin Alumni Research Foundation.

1. Dry the composite core material under vacuum for 24 hours.
2. Set atomization pressure of the Wurster fluidized bed coater apparatus to approximately 25 psig set the temperature controller to 20° C.; set filter pressure to 50 psig; set pulse frequency to 1 pulse/2.5 seconds; set to 20 RPM approximately 6.6 ml/min.; and set the air flow to give a pressure reading of 0.1 +/−0.02 inches water.
3. Load 400-600 g of levonorgestrel composite core material into the coating chamber.
4. Coat composite core material to 9% +/−3%.
5. Run the Wurster appartus under the following conditions: inlet temperature 72°–74° F.; Chamber temperature 66°–69° F.; outlet temperature 64°–67° F.; room temperature <74° F.; relative humidity 40–50%; solution flow rate ~6.6; atomizing air pressure ~25 psig; fluidizing air rate 0.2–0.5 CFM; plenum pressure 40 psig; filter pressure 50 psig; polymer viscosity ~1 dl/g; and core material 10% polymer, 90% levonorgestrel.
6. Continue for five minutes following addition of all soltuion and recover levonorgestrel-containing microparticles.

PROCEDURES FOR POST TREATMENT OF MICROCAPSULES

Dry Sieving:
1. Take all the microcapsules and sieve the entire batch using the ATM sonic sifter with a greater than 150 micron sieve.
2. Repeat three times with the material greater than 150 microns.
3. Replace the 150 micron sieve with the 106 micron sieve.
4. Take the less than 150 micron material and sieve the entire batch.
5. Repeat three times with the material greater than 106 microns.

Wet Sieving:
1. Take the 106-150 microns material and divide it into 50 gram batches.
2. Take one of the 50 gram batches and place it in a 400 ml beaker. 3. Add 200 ml of distilled water.
4. Stir with a spatula until capsules wet.
5. Place on an 8-inch round 106 micron sieve in a collection bucket.
6. Pour the wet capusles into a 106 micron 8-inch round sieve.
7. Set the Millipore distilled water tank sprayer at 50 psig.
8. Spray the capsules with distilled water at a distance of 6 inches for five minutes.
9. Empty the wet capsules into a 400 ml beaker.
10. Repeat steps 4 through 8.
11. Empty the wet-sieved capsules onto a 45 micron 8-inch round sieve.
12. Repeat steps 2 through 11 until all the dry sieved capsules are wet sieved.
13. Place the 45 micron sieve into a vacuum desiccator and dry to constant weight.

The 106-150 microcapsules are then packaged and stored in containers for use.

FIG. 1 illustrates the constnt release of the levonorgestrel from about 106-105 micron levonorgestrel-coated microparticles prepared as set forth illustrating a constant release in this particular case of over 200 days.

Figure 2:
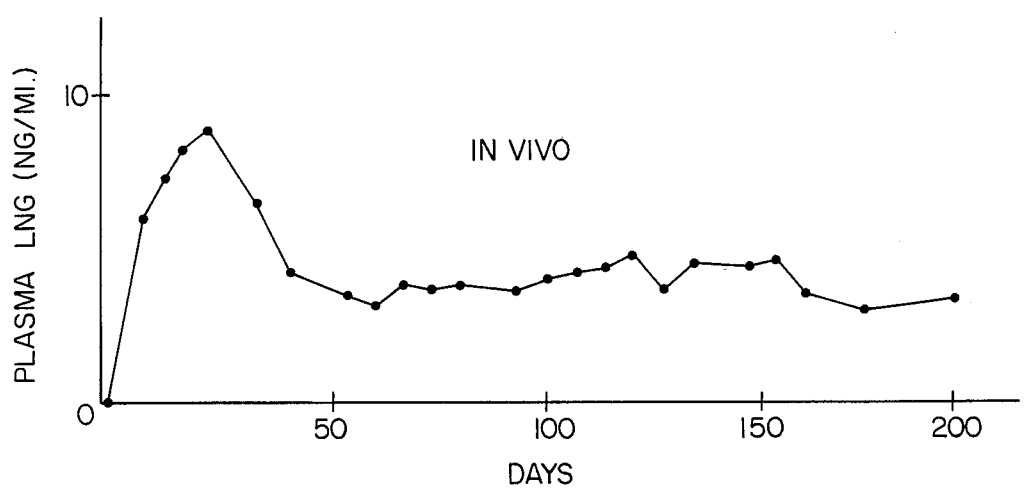
FIG. 2 is a graphical illustration of the constant in vivo release of the drug levonorgestrel from coated microparticles prepared by the process of the invention.

FIG. 2 illustrates the mean serum level in rabbits which were intramuscularly injected with the coated microparticles. The three rabbits intramuscularly implanted with the same coated microparticles as tested in FIG. 1 and in vivo mean serum level of levonorgesterol determined in the rabbits.

FIGS. 1 and 2 illustrate the constant uniform release of the coated drug from the coated microparticles, both in vivo and in vitro.

A wide variety of active ingredients with various coating polymers were used to prepare coated microparticles employing the process as described. The present active ingredient in the composite core particles ranged from 5 to 95% by weight. The process permitted the preparation of coated microparticles with large amounts of the active ingredient, for example, over 70%, and also permitted the use of admixtures wherein a less expensive material like chloresterol is used as a diluent for a very expensive drug such as levonorgestrel to provide sufficient bulk for coating. Some of the active ingredients of the core material and the coating polymer which were also used in the core material are set forth as follows:

| Core Material: | Coating Polymer: |
| --- | --- |
| 1. fire retardant - ammonium phosphate cariostatic | ethyl cellulose resin |
| 2. sodium fluoride | ethyl cellulose resin |
| 3. vitamin - sodium ascorbate | polylactide |
| 4. amino acid - tyrosine | polylactide |
| 5. contraceptive - chloresterol/levonorgestrel | polylactide |
| 6. contraceptive - norethindrone (10% slurry) | polylactide |
| 7. anesthetic - Lidocaine HCl | polylactide |
| 8. anesthetic - Etidocaine HCl | polylactide |
| 9. anesthetic - Bupivacaine HCl | polylactide |
| 10. anesthetic - Lidocaine Base | polylactide |
| 11. antiseptic - Povidone | polylactide |

-continued

| Core Material: | Coating Polymer: |
| --- | --- |
| 12. Iodine spermicide - Nonoxynol-9 | polyvinyl alcohol |
| 13. hormones - Testosterone | polylactide |
| 14. hormones - Progesterone | polylactide |

What is claimed is:

1. A microparticle suitable for the controlled release of an active ingredient, which microparticle comprises:
   (a) a solid composite core material comprising a uniform dispersion of a finely-divided active ingredient and a film-forming polymer, the active ingredient present in an amount of from about 5% to 95% by weight of the core material;
   (b) a generally uniform outer wall coating about the composite core material in a wall thickness, to provide for the desired controlled release of the active ingredient, said outer wall coating comprising a film-forming polymer the same or substantially the same as the said film-forming polymer in the core material, to provide for bonding of the wall coating of the film-forming polymer to the core material; and
   (c) the microparticle less than about 1000 microns in size.

2. A microparticle suitable for the controlled release of an active ingredient, which microparticle comprises:
   (a) a solid composite core material comprising a uniform dispersion of a finely-divided active drug ingredient, which drug ingredient comprises a hydrophobic steroid drug, and a film-forming polymer which comprises a biodegradable polymer selected from the group consisting of a polylactide, a polyglycolide, or a copolymer of lactide or glycolide, the active drug ingredient present in an amount of from about 5% to 95% by weight of the core material;
   (b) a generally uniform outer wall coating about the composite core material in a wall thickness, to provide for the desired controlled release of the active ingredient, said outer wall coating comprising a film-forming polymer the same or substantially the same as the said film-forming polymer in the core material, to provide for bonding of the wall coating of the film-forming polymer to the core material; and
   (c) the microparticle less than about 200 microns in size.

3. The microparticle of claim 1 which is less than about 200 microns in size.

4. The microparticles of claim 1 wherein the film-forming polymer is selected from the group consisting of a biodegradable polymer, polyvinyl alcohol, and cellulose material.

5. The microparticle of claim 1 wherein the film-forming polymer comprises biodegradable polymer selected from the group consisting of a polylactide, a polyglycolide, or a copolymer of lactide or glycolide.

6. The microparticle of claim 1 wherein the active ingredient is a hydrophobic steroid drug.

7. The microparticle of claim 1 wherein the active ingredient is a drug selected from the group consisting of testosterone, progesterone, nonoxynol-9, povidone iodine, cholesterol, levonorgestrel, tyrosine, norethindrone, lidocaine, etidocaine and bupivcaine.

8. The microparticle of claim 1 wherein the active ingredient comprises from about 20% to 80% by weight of the composite core mateial.

9. The microparticle of claim 1 wherein the outer wall coating thickness is from about 0.1 to 20 microns.

* * * * *